United States Patent
Dace et al.

(10) Patent No.: US 11,980,426 B2
(45) Date of Patent: May 14, 2024

(54) SYSTEM AND METHOD FOR PRELIMINARY REGISTRATION

(71) Applicant: WARSAW ORTHOPEDIC, INC., Warsaw, IN (US)

(72) Inventors: Mark C. Dace, Collierville, TN (US); Jeffrey Lynn Gum, Crestwood, KY (US)

(73) Assignee: WARSAW ORTHOPEDIC, INC., Warsaw, IN (US)

(*) Notice: Subject to any disclaimer, the term of this patent is extended or adjusted under 35 U.S.C. 154(b) by 706 days.

(21) Appl. No.: 16/983,835

(22) Filed: Aug. 3, 2020

(65) Prior Publication Data
US 2022/0031397 A1 Feb. 3, 2022

(51) Int. Cl.
*A61B 34/20* (2016.01)
*A61B 6/00* (2006.01)
(Continued)

(52) U.S. Cl.
CPC ............. *A61B 34/20* (2016.02); *A61B 6/487* (2013.01); *A61B 34/30* (2016.02); *A61B 90/39* (2016.02); *G06T 1/0014* (2013.01); *G06T 7/0012* (2013.01); *G06T 7/30* (2017.01); *G06T 7/70* (2017.01); *A61B 17/32093* (2013.01); *A61B 2034/2065* (2016.02); *A61B 2090/3937* (2016.02); *A61B 2090/3966* (2016.02);
(Continued)

(58) Field of Classification Search
CPC ... A61B 90/00; A61B 90/39; A61B 17/32093; A61B 17/29; A61B 17/320016; A61B 17/32002; A61B 34/20; A61B 34/30
See application file for complete search history.

(56) References Cited

U.S. PATENT DOCUMENTS

| | | |
|---|---|---|
| 6,430,434 B1 | 8/2002 | Mittelstadt |
| 6,764,217 B2 | 7/2004 | Yasuda et al. |
| (Continued) | | |

FOREIGN PATENT DOCUMENTS

| | | |
|---|---|---|
| CN | 102300512 | 12/2011 |
| CN | 104123540 | 9/2015 |
| (Continued) | | |

OTHER PUBLICATIONS

Guéziec et al. "Anatomy-Based Registration of CT-Scan and Intraoperative X-Ray Images for Guiding a Surgical Robot," IEEE Transactions on Medical Imaging, Oct. 1998, vol. 17, No. 5, pp. 715-728.
(Continued)

*Primary Examiner* — Vi X Nguyen
(74) *Attorney, Agent, or Firm* — Sheridan Ross P.C.

(57) ABSTRACT

Methods and systems for performing a preliminary registration is provided. Image data corresponding to an image depicting a tracking device and an anatomical element may be received. Robot positional data corresponding to a position of a robot may also be received. The robot and the anatomical element may be located in a common three-dimensional coordinate system based on the image data and the positional data to yield a preliminary registration. A suggested robot position may be determined based on the preliminary registration and a dimensional reach of a robot arm of the robot.

19 Claims, 5 Drawing Sheets

(51) Int. Cl.
  *A61B 34/30* (2016.01)
  *A61B 90/00* (2016.01)
  *G06T 1/00* (2006.01)
  *G06T 7/00* (2017.01)
  *G06T 7/30* (2017.01)
  *G06T 7/70* (2017.01)
  *A61B 17/3209* (2006.01)

(52) U.S. Cl.
  CPC ... *A61B 2090/3983* (2016.02); *G06T 2200/04* (2013.01); *G06T 2207/30088* (2013.01)

(56) References Cited

U.S. PATENT DOCUMENTS

| | | |
|---|---|---|
| 6,837,892 B2 | 1/2005 | Shoham |
| 6,856,826 B2 | 2/2005 | Seeley et al. |
| 7,139,418 B2 | 11/2006 | Abovitz et al. |
| 7,458,977 B2 | 12/2008 | McGinley et al. |
| 7,547,307 B2 | 6/2009 | Carson et al. |
| 7,634,306 B2 | 12/2009 | Sarin et al. |
| 8,031,922 B2 | 10/2011 | Haimerl et al. |
| 8,073,530 B2 | 12/2011 | Solar et al. |
| 8,311,611 B2 | 11/2012 | Csavoy et al. |
| 8,457,719 B2 | 6/2013 | Moctezuma de la Barrera et al. |
| 8,694,075 B2 | 4/2014 | Groszmann et al. |
| 8,721,660 B2 | 5/2014 | Ulfarsson et al. |
| 8,768,437 B2 | 7/2014 | Barrick |
| 9,008,756 B2 | 4/2015 | Cohen et al. |
| 9,125,556 B2 | 9/2015 | Zehavi et al. |
| 9,833,292 B2 | 12/2017 | Kostrzewski et al. |
| 10,034,713 B2 | 7/2018 | Yang et al. |
| 10,206,749 B2 | 2/2019 | Cleary et al. |
| 10,231,642 B2 | 3/2019 | Coste-Maniere et al. |
| 10,500,006 B2 | 12/2019 | Devengenzo et al. |
| 10,546,396 B2 | 1/2020 | Eichler et al. |
| 10,575,906 B2 | 3/2020 | Wu |
| 10,646,283 B2 | 5/2020 | Johnson et al. |
| 2003/0120283 A1 | 6/2003 | Stoianovici et al. |
| 2005/0027193 A1 | 2/2005 | Mitschke et al. |
| 2009/0080737 A1 | 3/2009 | Battle et al. |
| 2009/0093820 A1* | 4/2009 | Trieu ............... A61B 17/701 606/264 |
| 2009/0306499 A1 | 12/2009 | Van Vorhis et al. |
| 2011/0160589 A1 | 6/2011 | Fu et al. |
| 2013/0209208 A1 | 8/2013 | Bailey et al. |
| 2016/0296293 A1 | 10/2016 | Gill et al. |
| 2017/0245944 A1 | 8/2017 | Crawford et al. |
| 2017/0340389 A1 | 11/2017 | Otto et al. |
| 2017/0360512 A1 | 12/2017 | Couture et al. |
| 2018/0092699 A1 | 4/2018 | Finley |
| 2018/0153621 A1 | 6/2018 | Duindam et al. |
| 2018/0214225 A1 | 8/2018 | Hourtash et al. |
| 2018/0338804 A1 | 11/2018 | Azizian et al. |
| 2019/0021795 A1 | 1/2019 | Crawford et al. |
| 2019/0069963 A1 | 3/2019 | Azizian et al. |
| 2019/0070731 A1 | 3/2019 | Bowling et al. |
| 2019/0192233 A1 | 6/2019 | O'Grady et al. |
| 2019/0298277 A1 | 10/2019 | Zhang et al. |
| 2019/0350657 A1* | 11/2019 | Tolkowsky ............ A61B 46/20 |
| 2019/0380792 A1* | 12/2019 | Poltaretskyi .......... A61B 34/76 |
| 2020/0121331 A1 | 4/2020 | Morris et al. |

FOREIGN PATENT DOCUMENTS

| | | |
|---|---|---|
| CN | 109496143 | 3/2019 |
| WO | WO 2017/139621 | 8/2017 |
| WO | WO 2019/099346 | 5/2019 |
| WO | WO 2019/0245818 | 12/2019 |
| WO | WO 2020/047051 | 3/2020 |
| WO | WO 2020/072398 | 4/2020 |

OTHER PUBLICATIONS

Jun et al. "Using Optical Tracking for Kinematic Testing of Medical Robots," International Journal of Medical Robotics and Computer Assisted Surgery, Apr. 2018, vol. 14, No. 2, article e1890, 8 pages.

Šuligoj et al. "Automated Marker Localization in the Planning Phase of Robotic Neurosurgery," IEEE Access, Jun. 2017, vol. 5, pp. 12265-12274.

Wang et al. "Spatial Registration for a Three-Arm Robot Assisted Mandible Reconstruction Surgery," Mathematical Problems in Engineering, 2015, vol. 2015, Article ID 689278, 11 pages.

* cited by examiner

SYSTEM AND METHOD FOR PRELIMINARY REGISTRATION

FIELD

The present technology is related generally to registration of a robot and a patient, and more particularly, to a preliminary registration performed prior to a full registration.

BACKGROUND

When a robot is used in connection with a surgical procedure, knowing the position of the robot relative to the patient allows the robot to be maneuvered properly during the surgical procedure. One way to know the position of a robot relative to a patient is through registration. Registration enables a coordinate system of the robot to be linked to a coordinate system of the patient, such that the precise position, relative to the patient, of the registered component is known. Registration can be conducted at a beginning stage of a surgical operation and can be a time- and resource-intensive process.

SUMMARY

Exemplary aspects of the present disclosure include:

A preliminary registration method according to at least one embodiment of the present disclosure comprises: receiving image data corresponding to an image depicting a tracking device and an anatomical element, the tracking device disposed on a surface of a patient; receiving robot positional data corresponding to a position of a robot; locating the robot and the anatomical element in a common three-dimensional (3D) coordinate system based on the image data and the positional data to yield a preliminary registration; and determining a suggested robot position based on the preliminary registration and a dimensional reach of a robotic arm of the robot.

Any of the aspects herein, wherein the tracking device comprises a fluoroscopy marker and a fiducial marker.

Any of the aspects herein, wherein the surface of the patient is non-sterile.

Any of the aspects herein, wherein the image data corresponds to a single image.

Any of the aspects herein, further comprising identifying a patient position based on the preliminary registration.

Any of the aspects herein, further comprising receiving a surgical plan having a planned trajectory of one or more medical devices, the planned trajectory comprising a suggested depth of insertion and a suggested angle of insertion for each of the one or more medical devices, and wherein the determining is further based on the surgical plan.

Any of the aspects herein, further comprising determining a suggested location for attachment of the robot to the patient based on the preliminary registration and the surgical plan.

Any of the aspects herein, further comprising determining a suggested incision size and suggested incision position based on the preliminary registration and the surgical plan.

Any of the aspects herein, further comprising determining a suggested incision start point and a suggested incision end point based on the planned trajectory and the suggested incision size.

Any of the aspects herein, further comprising causing the robotic arm to indicate the suggested incision start point and the suggested incision end point.

Any of the aspects herein, wherein the robot comprises the robotic arm and a second robotic arm, the method further comprising causing the robotic arm to indicate the suggested incision start point and the second robotic arm to indicate the suggested incision end point.

A preliminary registration method according to at least one embodiment of the present disclosure comprises: positioning a tracking device near a planned surgical site on a patient, the tracking device having a first tracker and a second tracker; receiving image data depicting the first tracker and an anatomical element; receiving second tracker positional data corresponding to a position of the second tracker and robot positional data corresponding to a position of a robot; locating the robot and the anatomical element in a common three-dimensional (3D) coordinate system based on the image data, the second tracker positional data, and the robot positional data to yield a preliminary registration; and determining a suggested robot position based on the preliminary registration and a dimensional reach of the robot.

Any of the aspects herein, wherein the first tracker is a fluoroscopy marker and the second tracker is a fiducial marker.

Any of the aspects herein, wherein the second tracker positional data and the robot positional data are received from a navigation system.

Any of the aspects herein, further comprising receiving a surgical plan, and wherein the determining is further based on the surgical plan.

Any of the aspects herein, further comprising determining a planned trajectory of one or more medical devices based on the surgical plan, the planned trajectory comprising a suggested depth of insertion and a suggested angle of insertion for each of the one or more medical devices.

Any of the aspects herein, further comprising determining a suggested incision size and suggested incision position based on the preliminary registration and the surgical plan.

Any of the aspects herein, wherein the image data corresponds to a single image received from a fluoroscope.

A system for preliminary registration according to at least one embodiment of the present disclosure comprises: a tracking device configured to rest on a non-sterile surface of a patient's skin; at least one processor; and at least one memory storing instructions for execution by the at least one processor that, when executed, cause the at least one processor to: receive a surgical plan corresponding to a planned surgical procedure; receive image data corresponding to an image depicting the tracking and an anatomical element of the patient; receive robot positional data corresponding to a position of a robot; locate the robot and the anatomical element in a common three-dimensional (3D) coordinate system based on the image data and the positional data to yield a preliminary registration; and determine a suggested robot position based on the location of the robot in the 3D coordinate system, a dimensional reach of the robot, and the surgical plan.

Any of the aspects herein, wherein the image data is fluoroscopic image data and the image is two-dimensional.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
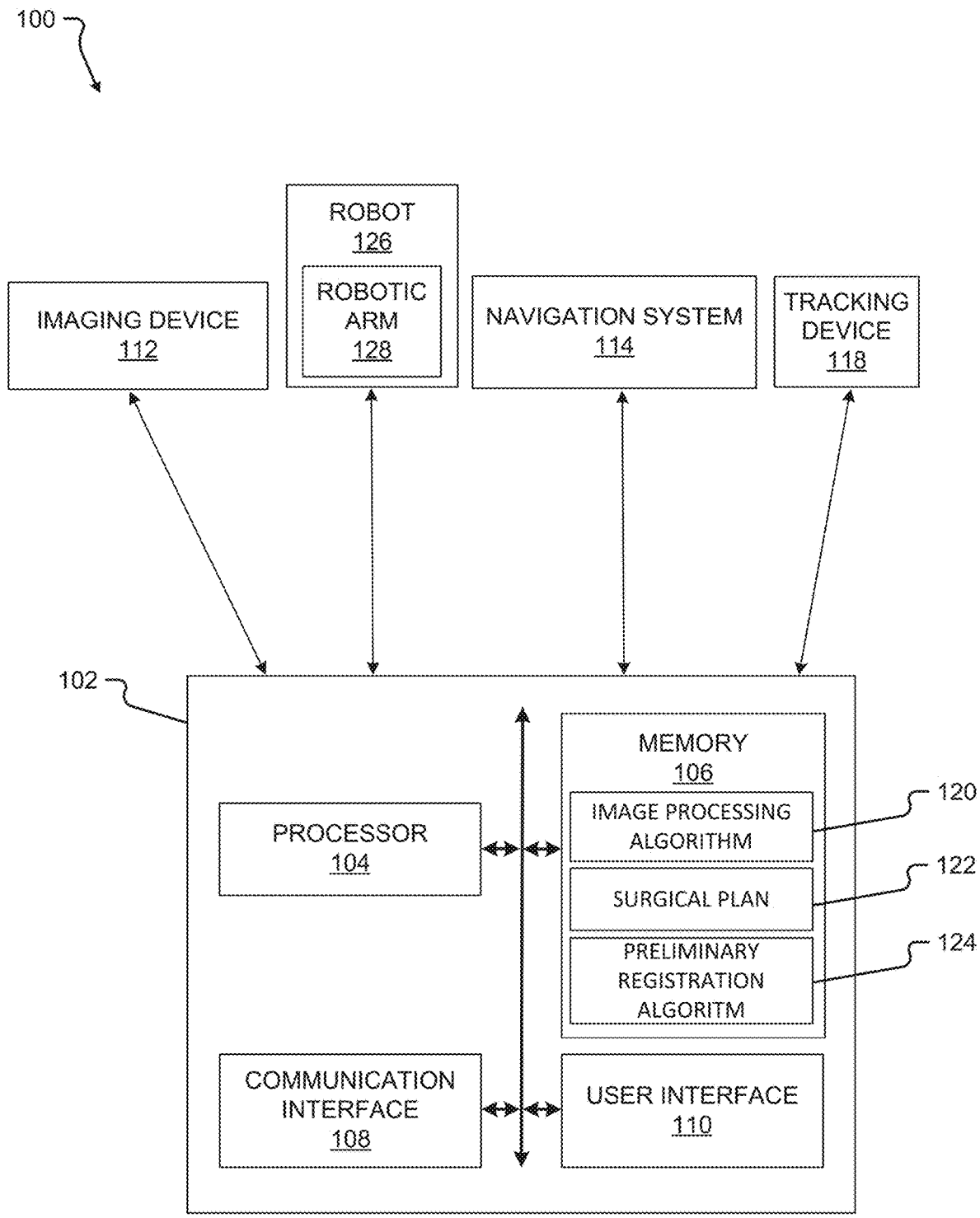
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Registration orients a robot to the patient in three-dimensional (3D) space. Until registration is complete, much useful information about, for example, robot positioning, incision planning, incision size, robot reach, and bone mount optimization is unavailable. Sometimes, this information, once obtained, necessitates repeating the registration process, thus increasing the time, money, and other resources needed for the operation. For example, where such information indicates that a position of the robot must be changed to successfully carry out a surgical procedure (e.g., because the robot cannot reach far enough to carry out a given aspect of the surgical procedure), the registration must be repeated after the robot has been moved.

Embodiments of the present disclosure comprise or utilize a "preliminary registration" performed after the patient and the robot are both placed on an operating table, but before a normal or full registration procedure that yields the accuracy required for surgery. The preliminary registration enables information about, for example, robot positioning, incision planning, incision size, robot reach, and bone mount optimization to be obtained prior to the full registration process. The present disclosure thus enables a more efficient preoperative workflow by reducing the likelihood that a full registration process will have to be repeated based on information obtained after the full registration process is complete. Benefits of the present disclosure include improved incision planning and optimization, robot mounting optimization, and fewer workflow challenges based on the sub-optimal execution of these steps.

According to at least some embodiments of the present disclosure, using existing navigation capabilities, one lateral fluoroscopy x-ray image, and one locator instrument, an orientation algorithm may be run to provide a relative location between the robot and a patient, for example, on a 3D coordinate system. Using the 3D coordinate system, a preoperative plan and the patient's position may be leveraged to indicate, for example, an optimal or recommended: robot attachment position on the table (based, for example, on robot reach); skin incision location and length (using, for example, either arm guidance or a navigated probe); and/or a robot/patient bone attachment location and suggested equipment.

The data obtained during a preliminary registration process according to embodiments of the present disclosure may be accurate enough to position the robot on the table optimally, locate a skin incision, and confirm that all relevant portions of a patient's anatomy are able to be reached with the limited stretch of a robot arm. Such data may not, however, be accurate enough to place screws. Even so, the present disclosure may beneficially enable a smaller skin incision, more efficient workflow, and less equipment-related manipulation.

One or more embodiments of the present disclosure may include, when used in connection with a spinal surgery, one or more of the following steps: placing a patient and a robot on an operating table; setting a registration tracker on top of the patient's skin, for example on a midline of the patient's spine and in the general area of surgery; taking a lateral fluoroscopy picture, including the spine anatomy and the registration tracker; ensuring that a navigation camera sees the registration tracker, an existing snapshot tracker on a robot arm of the robot, and a robot reference frame; running an algorithm (e.g., with a computer) that locates the patient's vertebrae, the reference tracker, and the robot arm via the snapshot tracker in a common 3D coordinate system; and determining, using the 3D coordinate system and based on a preoperative plan and the patient's position, an optimal or recommended: robot attachment position on the table (based on robot reach), skin incision location and length (using either arm guidance or navigated probe), and/or robot/patient bone attachment location and suggested equipment; marking a position/length of a recommended skin incision based on screw projections at skin level (e.g., based on a trajectory calculated based on the preoperative plan); moving the robot on the table to the suggested location; finishing preparing/draping the patient and the robot; attaching the robot to the patient; making an incision at the previously marked location; fully registering the robot to the patient for robotic guidance/screw placement; and/or placing the screws.

Embodiments of the present disclosure also provide for a registration tracker or tracking device that rests on a patient's non-sterile skin. In other words, the registration tracker need not be mounted to a bone of the patient, and therefore does not require sterilizing the patient's skin, making an incision, or securing the registration tracker to a bone through the incision. The tracker or tracking device may have navigation tracking spheres and fluoroscopy registration markers. The tracker or tracking device allows for rough (e.g., preliminary) registration with only one fluoroscopy image and navigated marker to enable optimized process steps that were previously inaccessible.

As described more fully below, methods and systems for performing a preliminary registration according to at least some embodiments of the present disclosure may beneficially determine a suggested robot position on a surgical table and/or relative to a patient based on a preliminary registration using image data of a tracker or tracking device and of an anatomical element and robot position data.

Turning first to FIG. 1, a block diagram of a system 100 according to at least one embodiment of the present disclosure is shown. The system 100 may be used to process image data; execute a preliminary registration algorithm and/or an image processing algorithm; and/or carry out other aspects of one or more of the methods disclosed herein. The system 100 comprises a computing device 102, one or more imaging devices 112, a navigation system 114, a robot 126, and/or one or more tracking devices 118. Systems according to other embodiments of the present disclosure may comprise more or fewer components than the system 100. For example, the system 100 may not include the navigation system 114 and/or the robot 126.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 126, and/or the navigation system 114.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the method 300 described herein. The memory 106 may store, for example, one or more image processing algorithms 120, one or more preliminary registration algorithms 124, and/or one or more surgical plans 122. Such algorithms may, in some embodiments, be organized into one or more applications, modules, packages, layers, or engines. The algorithms may cause the processor 104 to manipulate data stored in the memory 106 and/or received from the imaging device 112, the robot 126, and/or the navigation system 114.

The computing device 102 may also comprise a communication interface 108. The communication interface 108 may be used for receiving image data or other information from an external source (such as the imaging device 112, the navigation system 114 and/or the robot 126), and/or for transmitting instructions, images, or other information to an external system or device (e.g., another computing device 102, the navigation system 114, the imaging device 112, and/or the robot 126). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, headset, and/or any other device for receiving information from a user and/or for providing information to a user. In some embodiments, the user interface 110 may receive information and/or commands from a user via voice activation. In other embodiments, the user interface 110 may incorporate augmented reality or virtual reality. The user interface 110 may be used, for example, to receive a user selection or other user input regarding positioning a tracking device 118 near a planned surgical site on a patient, the tracking device 118 having a first tracker and a second tracker; to receive a user selection or other user input regarding image data corresponding to an image depicting a tracking device 118 and an anatomical element; to receive a user selection or other user input regarding image data corresponding to an image depicting the first tracker and an anatomical element; to receive a user selection or other user input regarding robot positional data corresponding to a position of a robot; to receive a user selection or other user input regarding second tracker positional data corresponding to a position of the second tracker; to receive user input regarding locating a robot and an anatomical element in a common three-dimensional (3D) coordinate system to yield a preliminary registration; to receive a user selection or other user input regarding determining a suggested robot position based on the preliminary registration; to receive a user selection or other user input regarding identifying a patient position based on the preliminary registration; and/or to display the image data and/or the surgical plan 122. In some embodiments, the user interface 110 may be useful to allow a surgeon or other user to modify the plan 122, or other information displayed, though it will be appreciated that each of the preceding inputs may be generated automatically by the system 100 (e.g., by the processor 104 or another component of the system 100) or received by the system 100 from a source external to the system 100. In some embodiments, user input such as that described above may be optional or not needed for operation of the systems, devices, and methods described herein.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image a patient and/or the tracking device 118 to yield an image and/or image data. The imaging device 112 may be capable of taking a 2D image or a 3D image to yield the image data. "Image data" as used herein refers to the data generated or captured by an imaging device, including in a machine-readable form, a graphical form, and in any other form. In various examples, the image data may comprise data corresponding to an anatomical feature of the patient or a portion thereof (e.g., a spinal region) and/or the tracking device 118. The imaging device 112 may be or comprise, for example, a fluoroscope, but may also be or comprise an ultrasound probe, an O-arm, a C-arm, a G-arm, or any other device utilizing X-ray-based imaging (e.g., a CT scanner, or other X-ray machine), a magnetic resonance imaging (MRI) scanner, an optical coherence tomography scanner, an endoscope, a telescope, a thermographic camera (e.g., an infrared camera), or any other imaging device suitable for obtaining images or image data corresponding to an anatomical feature of a patient and/or a tracking device 118.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, a snapshot tracker, the tracking device 118, or other objects within the operating room or other room where a surgery takes place. In various embodiments, the navigation system 114 may be used to track a position of the imaging device 112 (or, more particularly, of a navigated reference marker attached, directly or indirectly, in fixed relation to the imaging device 112), of the tracking device 118 (via a navigated reference marker thereof), and/or of the robot 126 (or, more particularly, of a navigated reference marker attached, directly or indirectly, in fixed relation to the robot 126). The navigation system 114 may include a display for displaying one or more images from an external source (e.g., the computing device 102, imaging device 112, or other source) or a video stream from the camera or other sensor of the navigation system 114.

In some embodiments, the navigation system 114 may be used to track movement of the robot 126 and may provide feedback regarding or confirmation of a position of the robot 126. For example, the navigation system 114 may indicate—audibly and/or visually via a display—that the robot 126 needs to be moved, automatically or manually, to a suggested robot position. The navigation system 114 can monitor or track the robot 126 as the robot 126 is moved toward the suggested robot position based, in part, on the tracking device 118, which remains stationary on the patient 202. The navigation system 114 can further indicate to or alert a user when the robot 126 has reached the suggested robot position. In other embodiments, a user may view a display of the navigation system 114 while moving the robot 126 to the suggested robot position, so as to ensure that the user moves the robot 126 to the correct position. In some embodiments, the system 100 can operate without the use of navigation system 114.

The robot 126 may be any surgical robot or surgical robotic system. The robot 126 may be or comprise, for example, the Mazor X™ Stealth Edition robotic guidance system. The robot 126 may comprise one or more robotic arms 128. In some embodiments, the robotic arm 128 may comprise a plurality of robotic arms, though the robot 126 may comprise one robotic arm, two robotic arms, or more than two robotic arms. In some examples, the robotic arms 128 may comprise a first robotic arm for supporting a first marker to mark a suggested incision start point and a second robotic arm for supporting a second marker to mark a suggested incision end point. In other examples, the first marker and the second marker may be held by the same robotic arm 128. The robotic arm 128 may have a dimensional reach that is a maximum distance that an end of the robotic arm 128 can reach to. In some embodiments, the dimensional reach is between 18 and 20 inches long. In other embodiments, the dimensional reach is equal to or less than 18 inches or equal to or greater than 20 inches. The robotic arm 128 may be used to selectively hold and/or operate one or more surgical tools, the imaging device 112, and/or any other tool or instrument.

Reference markers (i.e., navigation markers) may be placed on the robot 126, the robotic arm 128, the imaging device 112, or any other object in the surgical space. The reference markers may be tracked by the navigation system 114, and the results of the tracking may be used by the robot 126 and/or by an operator of the system 100 or any component thereof. As described above, in some embodiments, the navigation system 114 can be used to track other components of the system 100 (e.g., the imaging device 112) and the system 100 can operate without the use of the robot 126 (e.g., with the surgeon manually manipulating the imaging device 112). The reference marker may include the tracking device 118, which may be positioned on a patient for imaging during a preliminary registration.

Figure 2:
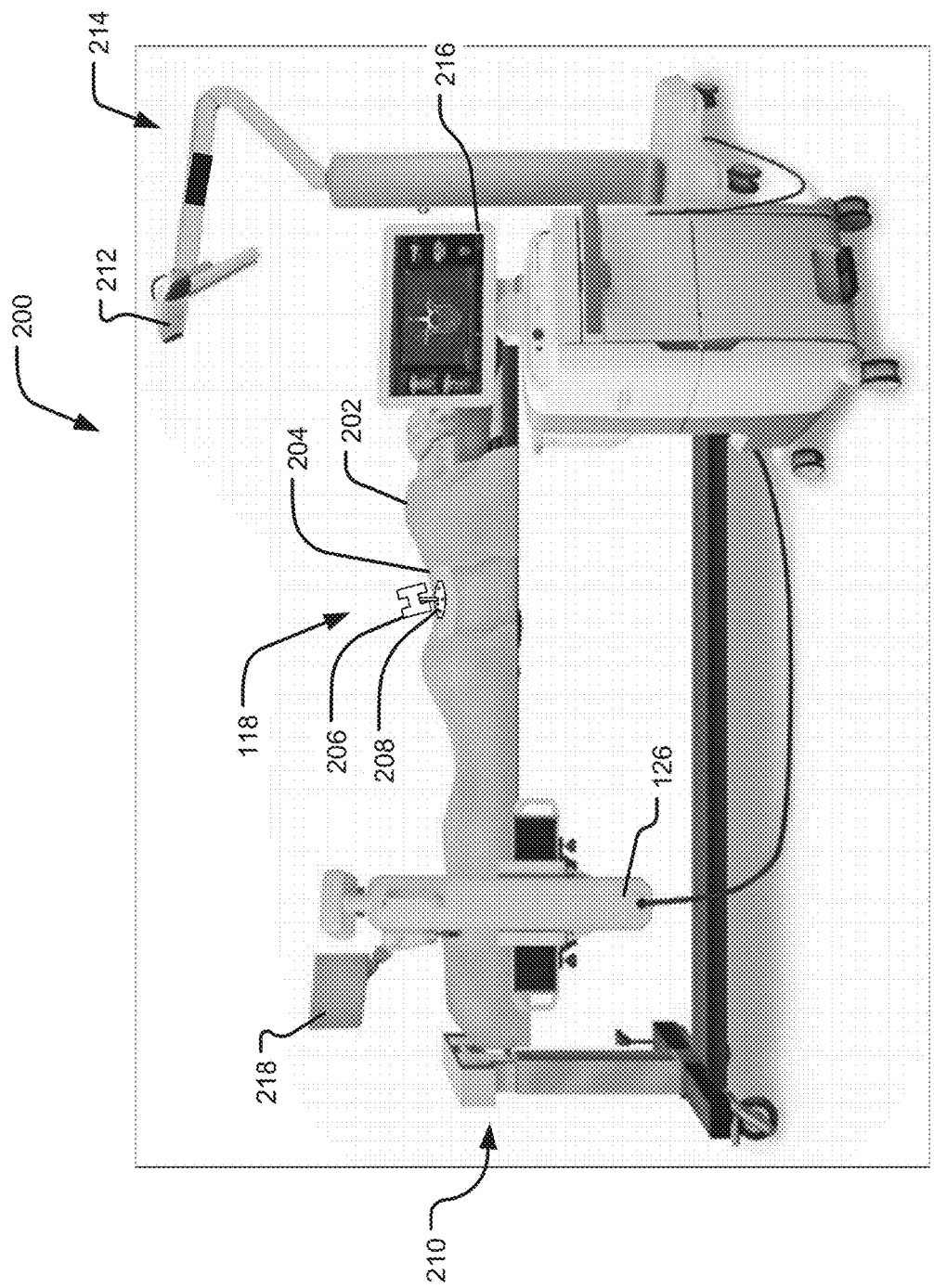
FIG. 2 is an image of a tracking device and a patient according to at least one embodiment of the present disclosure.

Turning to FIG. 2, at least a portion of a surgical room 200 is illustrated including a robot 126 coupled to an operating table 210, a patient 202 laying prone on the table 210, a navigation system 214 (which may be the same as or similar to the navigation system 114 described above). In this embodiment, the navigation system 214 comprises an imaging device 212 (which may be the same as or similar to the imaging device 112 described above), as well as a user interface 216 (e.g., a display), which may be the same as or similar to the user interface 110 described above.

In some embodiments, the tracking device 118 includes an alignment feature for aligning the tracking device 118 on the patient 202 or otherwise indicating where the tracking device 118 should be positioned and oriented on and/or relative to the patient 202. For example, in some embodiments, the alignment feature includes one or more arrows. The arrows may be used to align the tracking device 118 along a spine of the patient, for example. In other embodiments, the alignment feature includes one or more lines or other markings useful for instructing a user where and/or how to place the tracking device 118 on the patient, and/or for assisting a user to properly place and/or align the tracking device 118 on or relative to the patient.

In some embodiments, the tracking device 118 may include one tracker. In other embodiments, the tracking device 118 includes more than one tracker. As shown, the tracking device 118 may include a first tracker 206 and a second tracker 208. In some embodiments, the first tracker 206 is different from the second tracker 208 (e.g., such that the tracking device 118 is a hybrid tracker). For example, in some embodiments, the first tracker 206 is a fluoroscopy marker and the second tracker 208 is a fiducial marker. In such embodiments, the fluoroscopy marker may be detectable by a fluoroscope and visible in a fluoroscopy image and the fiducial marker may be detectable and/or tracked by a camera of the navigation system 114. The fluoroscopy marker may include metal spheres and the fiducial marker may include optical spheres. In other embodiments, the first tracker 206 may be the same as the second tracker 208.

As shown in the illustrated embodiment, the tracking device 118 may be positioned or disposed on a surface 204 of a patient's 202 skin. The surface 204 is non-sterile in some embodiments. In other embodiments, the surface 204 may be sterile. In either embodiment, the tracking device 118 beneficially need not be mounted to a bone of the patient, such that sterilization is not required, no incision needs to be made, and the tracking device 118 may simply be placed on the patient 202. The tracking device 118 may also therefore be easily moved from one location on the patient 202 to another location on the patient 202, if desired. The tracking device 118 is positioned close to or near a surgical site where a surgical procedure is to be performed. In the illustrated example, the tracking device 118 is positioned near a spinal region of the patient 202. In other examples, the tracking device 118 may be positioned elsewhere on the patient 202. In some embodiments, the tracking device 118 may comprise an adhesive to adhere the tracking device 118 to the skin, for example to enable the tracking device to be placed on a surface of the skin that is angled or otherwise oriented such that the tracking device 118 will not remain in place due to gravity and/or friction alone. In other embodiments, the tracking device 118 may comprise a non-slip surface that rests on the skin, again to reduce a chance of the tracking device 118 moving after being positioned. In still other embodiments, the tracking device may comprise a weighted base to ensure that the tracking device 118 remains upright while resting on the patient 202.

During use, the tracking device 118 is placed on the surface 204 of the patient 202 and an image of the tracking device 118 (as well as of a portion of the patient 202 proximate the tracking device 118) is then captured using the imaging device 212. Thereafter, the tracking device 118 may be removed from the patient 202. The tracking device 118 conveniently rests on the skin or other surface 204 of the patient 202 and is simple and quick to use.

Attached to the robot 126 as shown in FIG. 2 is a reference frame 218. The reference frame 218 is detectable by the navigation system 214 and enables the navigation system 214 to determine a position of the robot 126. Although not visible in FIG. 2, the robot 126 also comprises a robotic arm (which may be the same as or similar to the robotic arm 128 described above) to which a snapshot tracker is attached. Like the reference marker 218 with respect to the robot 126, the snapshot tracker on the robotic arm enables the navigation system 214 to determine a position of the robotic arm 128. The position of the robot 126 on the operating table 210 and relative to the patient 202 in FIG. 2 simply reflects an initial, preliminary positioning. The preliminary registration process described herein may be used to determine a recommended position of the robot 126, to which position the robot 126 may be moved following the preliminary registration process.

Figure 3:
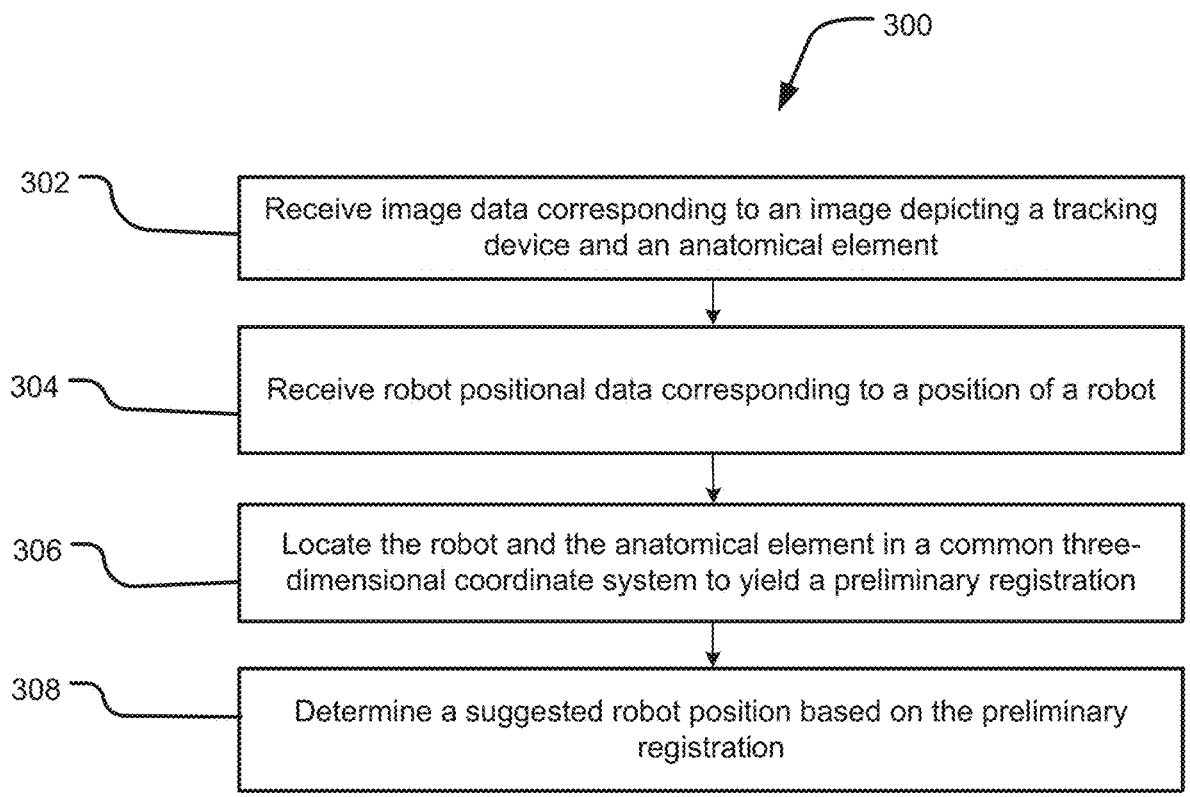
FIG. 3 is a flowchart of a method according to at least one embodiment of the present disclosure.

Turning now to FIG. 3, a method 300 for conducting a preliminary registration may be executed in whole or in part, for example, on a computing device such as the computing device 102 or similar device, and may utilize one or more other components of the system 100 or similar components. One or more aspects of the method 300 may be performed by or with a surgical robot, a surgeon, or a combination of both using one or more imaging devices such as the imaging device 112 or 212.

The method 300 comprises receiving image data corresponding to an image (step 302). In some embodiments, the image data corresponds to a single image. Also in some embodiments, the image data corresponds to a single, 2D image. In such embodiments, the single image may be received from a fluoroscope, an O-arm, a C-arm, or any other imaging device. The single image may be a lateral fluoroscopy image. In other embodiments, the image data may correspond to more than one image and may be received from one imaging device or more than one imaging device. The image data may be received via a user interface such as the user interface 110 or 216 and/or via a communication interface such as the communication interface 108 of a computing device such as the computing device 102, and may be stored in a memory such as the memory 106. The image data may also be generated by and/or uploaded to any other component of the system 100. In some embodiments, the image data may be generated by an imaging device such as the imaging device 112, and may be received directly from the imaging device, or indirectly via any other component of the system 100 or a node of a network to which the system 100 is connected. In such embodiments, the image data may be received via, for example, the communication interface.

The image may depict a tracking device, such as the tracking device 118, and an anatomical element of a patient. The image data may be processed using an image processing algorithm such as the imaging processing algorithm 120 to identify the anatomical element and the tracking device in the image. In some embodiments, feature recognition may be used to identify a feature of the anatomical element and/or of the tracking device. For example, a contour of a vertebrae may be identified in the image. In other embodiments, the image processing algorithm may use artificial intelligence or machine learning to identify the anatomical element and/or the tracking device.

The method 300 also comprises receiving robot positional data corresponding to a position of a robot, such as the robot 126 (step 304). The robot positional data may include coordinates from and/or an orientation of the robot and/or a robotic arm such as the robotic arm 128. The robot positional data may be relative to an operating table such as the operating table 210. In some embodiments, the robot positional data may be received from a navigation system such as the navigation system 114 or 214. The robot positional data may comprise image data, such as image data from a navigation system such as the navigation system 114 or 214. In other embodiments, the robot positional data may be received from the robot. For example, the robot may include positional sensors for tracking and transmitting a position of the robot to, for example, the computing device. In other embodiments, the robot positional data may be received through a user interface from a surgeon or operator.

The method 300 also comprises locating the robot and the anatomical element in a common 3D coordinate system based on the image data and the robot positional data to yield a preliminary registration (step 306). A preliminary registration algorithm such as the preliminary registration algorithm 124 may be configured to locate the robot and the anatomical element in the common 3D coordinate system. In some embodiments, the algorithm may be configured to locate the robot in the common 3D coordinate system by relating the known position of the robot to a position of the patient based on the tracking device and the anatomical element depicted in the image corresponding to the image data. The locating may comprise utilizing one or more image processing algorithms to analyze the image data received in the step 302 as well as any robot positional data that comprises image data. Also in some embodiments, the locating may comprise determining a position of the tracking device in a common 3D coordinate system based on the image data, determining a position of the robot in the common 3D coordinate system based on the robot positional data, and then determining a relative position of the robot to the patient based on the known position of the robot and the patient in the common 3D coordinate system.

The preliminary registration advantageously and quickly provides information to a surgeon early in the surgical procedure process. For example, the preliminary registration can be used to determine a recommended or an optimal position of the robot, as described below. The preliminary registration may also provide information about a position or alignment of the anatomical element (e.g., a position or alignment of a spine). Such position or alignment information may be used by the surgeon to position and/or orient the patient.

The method 300 further comprises determining a suggested robot position based on the preliminary registration and a dimensional reach of the robotic arm (e.g., the robotic arm 128) of the robot (step 308). The suggested robot position is a position at which the robot may be connected to the table to reach all levels or points needed for the surgical procedure, thereby reducing or eliminating the risk of needing to reposition the robot—including disconnecting the robot from the patient, moving the robot, and reconnecting the robot to the patient—if the robot is out of reach of certain levels or points. Where multiple possible positions of the robot would allow the robot to reach all levels or points needed for the surgical procedure, the suggested robot position may be or comprise a range of suggested positions. Alternatively, in such instances the suggested robot position may be a position that minimizes the amount the robotic arm will need to move during the surgical procedure, or that places the robot as far out of the way as possible while still enabling the robot to reach all needed levels or points, or that maximizes, minimizes, or otherwise optimizes one or more other considerations.

In instances where multiple robot positions are needed at different steps or stages of a surgical procedure (e.g., for surgical procedures covering an extended portion of a patient), the suggested robot position determined based on the preliminary registration may a position from which the robot can be easily moved to one or more subsequent suggested positions for a subsequent aspect of the surgical procedure. The subsequent suggested positions may be determined based on the preliminary registration, or based on a surgical plan, or based at least in part on one or more additional preliminary registrations. For example, a surgical robot may be secured to an operating table via a frame. The surgical robot may be selectively slidable along the frame, and the frame may be moveable from one position to another on the operating table. However, sliding the robot along the frame may be less time-intensive and/or easier than moving the frame from one position to another on the operating table. In this example, a first suggested robot position determined based on a first preliminary registration may comprise a suggested position for the frame on the operating table as well as a suggested position for the robot on the frame. The suggested position for the frame on the operating table may be a position from which the frame will not, or is unlikely to, need to be moved, even if the robot does need to be moved for one or more subsequent steps or stages of a surgical procedure. Similarly, the suggested position for the robot on the frame may be determined to increase a likelihood that any subsequent suggested positions of the robot can be reached merely by sliding the robot along the frame. In some embodiments, the determining step 308 may be further based on a surgical plan, as described in detail below.

Although described herein in connection with a robot that connects to an operating table, the method 300 may be used in connection with repositionable robots of any kind, including robots that are supported on a selectively moveable cart, robots supported entirely by a patient's body, and robots that may be selectively connected to a structure other than an operating table.

The method 300 may comprise, in some embodiments, receiving a surgical plan, which may be the same as or similar to the surgical plan 122. The surgical plan may be received via a user interface (e.g., the user interface 110) and/or a communication interface (e.g., the communication interface 108) of a computing device such as the computing device 102, and may be stored in a memory such as the memory 106 of the computing device 102. The surgical plan may include information about one or more planned movements of a tool held by the robotic arm during a surgical procedure. In some embodiments, the surgical plan includes a planned trajectory of one or more medical devices (e.g., medical tools, medical screws, medical plates, etc.). The information may also include a timeline or schedule of the one or more planned movements. The one or more planned movements may include one or more of timestamps, types of movement (e.g., translational and/or rotational), durations of movement, and/or positional information (e.g., starting, intermediate, and/or ending coordinates and/or orientation).

In some embodiments, the method 300 may comprise determining information about one or more needed movements of the tool during a surgical procedure outlined or otherwise described in a surgical plan. In such embodiments, the surgical plan may not include receiving any such information, whether via a computing device or otherwise, but a processor, executing instructions stored in a memory, may generate such information based on the surgical plan.

The determining step 308 may be further based on the surgical plan. For example, in some embodiments, the method 300, and more specifically the step 308, may comprise determining a planned trajectory of one or more medical devices (e.g., medical tools, medical screws, medical plates, etc.) based on the surgical plan. In such embodiments, the planned trajectory may comprise a suggested depth of insertion and a suggested angle of insertion for each of the one or more medical devices.

Figure 4:
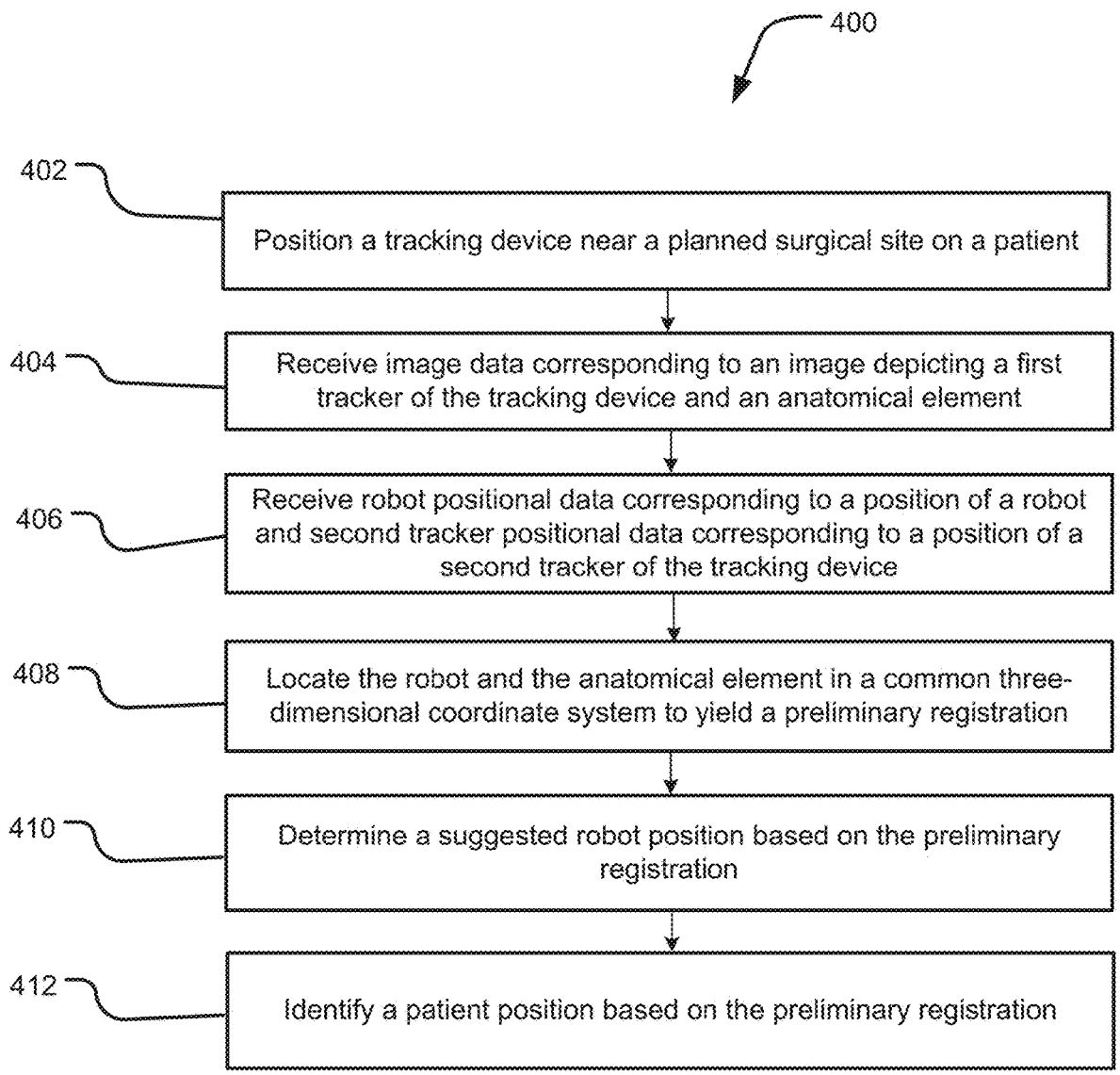
FIG. 4 is another flowchart of a method according to at least one embodiment of the present disclosure.

Turning now to FIG. 4, a method 400 for conducting a preliminary registration may be executed, for example, in whole or in part, on a computing device such as the computing device 102 or similar device, and may utilize one or more other components of the system 100 or similar components. One or more aspects of the method 400 may be performed by or with a surgical robot, a surgeon, or a combination of both using one or more imaging devices such as the imaging device 112 or 212.

The method 400 comprises positioning a tracking device, such as the tracking device 118, near a planned surgical site on a patient, such as the patient 202 (step 402). The tracking device may include a first tracker, such as the first tracker 206, and a second tracker, such as the second tracker 208. As previously described, the tracking device may be positioned or disposed on a surface of the patient's skin. The surface is non-sterile in some embodiments. In other embodiments, the surface may be sterile. In either embodiment, the tracking device beneficially need not be mounted to a bone of the patient, such that sterilization is not required, no incision needs to be made, and the tracking device may simply be placed on the patient. Further, because the tracking device is simply placed on the patient, the tracking device may be easily moved from one location on the patient to another location on the patient, if desired.

The method 400 comprises receiving image data corresponding to an image (step 404). In some embodiments, the image data corresponds to a single image. Also in some embodiments, the image data corresponds to a single, 2D image. Further, in some embodiments, the image data corresponds to a single lateral fluoroscopy image. In such embodiments, the single image may be received from a fluoroscope, an O-arm, a C-arm, or any other imaging device. In other embodiments, the image data may correspond to more than one image and may be received from one imaging device or more than one imaging device. The image data may be received via a user interface such as the user interface 110 or 216 and/or via a communication interface such as the communication interface 108 of a computing device such as the computing device 102, and may be stored in a memory such as the memory 106. The image data may also be generated by and/or uploaded to any other component of the system 100. In some embodiments, the image data may be generated by an imaging device such as the imaging device 112, and may be received directly from the imaging device, or indirectly via any other component of the system 100 or a node of a network to which the system 100 is connected. In such embodiments, the image data may be received via, for example, the communication interface.

The image may depict the tracking device and an anatomical element of a patient. In some embodiments, the image depicts the first tracker of the tracking device and the anatomical element of the patient. The image data may be processed using an image processing algorithm such as the imaging processing algorithm 120 to identify the anatomical element and the tracking device (or the first tracker) in the image. In some embodiments, feature recognition may be used to identify a feature of the anatomical element and/or of the tracking device. For example, a contour of a vertebrae may be identified in the image. In other embodiments, the image processing algorithm may use artificial intelligence or machine learning to identify the anatomical element and/or the tracking device.

The image data may be used to measure or otherwise calculate, for example, a distance measured between a surface of the skin of a patient (and/or of one or more features of the tracking marker) on the one hand and one or more bones depicted in the image data on the other. These or other measurements may be used, in turn, to recommend a tool size. The surface of the skin may be measured from a base of the tracking device. A surgeon, user, or a processor such as the processor 104 may determine or select a recommended tool size based on a known length of each tool and the measured distance. In some embodiments, a tool may be selected if the tool length (or other relevant dimension) is equal to or greater than the measured distance.

The method 400 also comprises receiving robot positional data corresponding to a position of a robot, such as the robot 126, and second tracker positional data corresponding to a position of a second tracker, such as the second tracker 208, of the tracking device (step 406). The robot positional data may include coordinates from and/or an orientation of the robot and/or a robotic arm such as the robotic arm 128. The robot positional data and/or the second tracker positional data may be relative to an operating table such as the operating table 210. The second tracker positional data may include coordinates of and/or an orientation of the second tracker of the tracking device. In some embodiments, the robot positional data and/or the second tracker positional data may be received from a navigation system such as the navigation system 114 or 214. The robot positional data and/or the second tracker positional data may comprise image data, such as image data from a navigation system (e.g., the navigation system 114 or 214). For example, a navigation system may be used to detect and/or determine a position of the robot (based on one or more tracking markers on the robot) and of the tracking device (based on the second tracker), and may then provide positional information corresponding to the position of the robot and of the tracking device to a processor. In some embodiments, the navigation system may provide raw data to the processor, which may then use the raw data to determine a robot position and a tracking device position.

In other embodiments, the robot positional data may be received from the robot. For example, the robot may include positional sensors for tracking and transmitting a position of the robot to, for example, the computing device. In still other embodiments, the robot positional data and/or the second tracker positional data may be received through a user interface from a surgeon or operator.

The method 400 also comprises locating the robot and the anatomical element in a common 3D coordinate system based on the image data, the robot positional data, and the second tracker position data to yield a preliminary registration (step 408). A preliminary registration algorithm such as the preliminary registration algorithm 124 may be configured to locate the robot and the anatomical element in the common 3D coordinate system. In some embodiments, the algorithm may be configured to locate the robot in the common 3D coordinate system by relating the known position of the robot to a position of the patient based on the tracking device and the anatomical element depicted in the image corresponding to the image data and the second tracker positional data. In other words, the algorithm may determine a correlation between the robot positional data and the second tracker positional data, a correlation between the robot positional data and the first tracker based on the known relationship of the second tracker to the first tracker, and a correlation between the first tracker and the anatomical element. The aforementioned correlations can be used to determine a correlation between the robot and the patient.

The locating may comprise utilizing one or more image processing algorithms to analyze the image data received in the step 404 as well as any robot positional data and/or second tracker positional data that comprises image data. Also in some embodiments, the locating may comprise determining a position of the first tracker in a common 3D coordinate system based on the image data, determining a position of the robot in the common 3D coordinate system based on the robot positional data, determining a position of the second tracker in the common 3D coordinate system based on the second tracker positional data, and then determining a relative position of the robot to the patient based on the known position of the robot and the patient in the common 3D coordinate system.

The preliminary registration advantageously and quickly provides information to a surgeon early in the surgical procedure process. For example, the preliminary registration can be used to determine a suggested or recommended position of the robot, as described below. The preliminary registration may also provide information about a position or alignment of the anatomical element (e.g., a position or alignment of a spine), also described below.

The method 400 further comprises determining a suggested robot position based on the preliminary registration and a dimensional reach of the robotic arm (e.g., the robotic arm 128) of the robot (step 410). The suggested robot position is a position at which the robot may be connected to the table to reach all levels or points needed for the surgical procedure, thereby reducing or eliminating the risk of needing to reposition the robot if the robot is out of reach of certain levels or points. Where multiple possible positions of the robot would allow the robot to reach all levels or points needed for the surgical procedure, the suggested robot position may be or comprise a range of suggested positions. Alternatively, in such instances the suggested robot position may be a position that minimizes the amount the robotic arm will need to move during the surgical procedure, or that places the robot as far out of the way as possible while still enabling the robot to reach all needed levels or points, or that maximizes, minimizes, or otherwise optimizes one or more other considerations.

In some embodiments, the determining step 410 may be further based on a surgical plan. For example, in some embodiments, the method 400, and more specifically the step 410, may comprise determining a planned trajectory of one or more medical devices (e.g., medical tools, medical screws, medical plates, other implants) based on the surgical plan. In such embodiments, the planned trajectory may comprise a suggested depth of insertion and a suggested angle of insertion for each of the one or more medical devices. The determining step 410 may also include determining the suggested position of the robot so as to ensure that the robot can achieve the planned trajectory for each of the one or more medical devices.

The method 400 further comprises identifying a patient position based on the preliminary registration (step 412). The preliminary registration may be used to identify vertebral bodies and to calculate one or more measurements related to the identified vertebral bodies (e.g., parameters for lumbar lordosis or sagittal alignment). Information corresponding to such vertebral bodies and/or measurements may be communicated to a surgeon to indicate a patient position to the surgeon. The surgeon may then use the information to position, reposition, adjust, and/or orient the patient. For example, the surgeon may use information about the patient position to move the patient, to add, move, or remove pillows that affect the patient position, and/or to adjust the table to achieve a desired patient position and spinal alignment. The information may be taken into account when determining the suggested or recommended position of the robot.

Although described herein in connection with a robot that connects to an operating table, the method 400 may be used in connection with repositionable robots of any kind, including robots that are supported on a selectively moveable cart, robots supported entirely by a patient's body, and robots that may be selectively connected to a structure other than an operating table.

Figure 5:
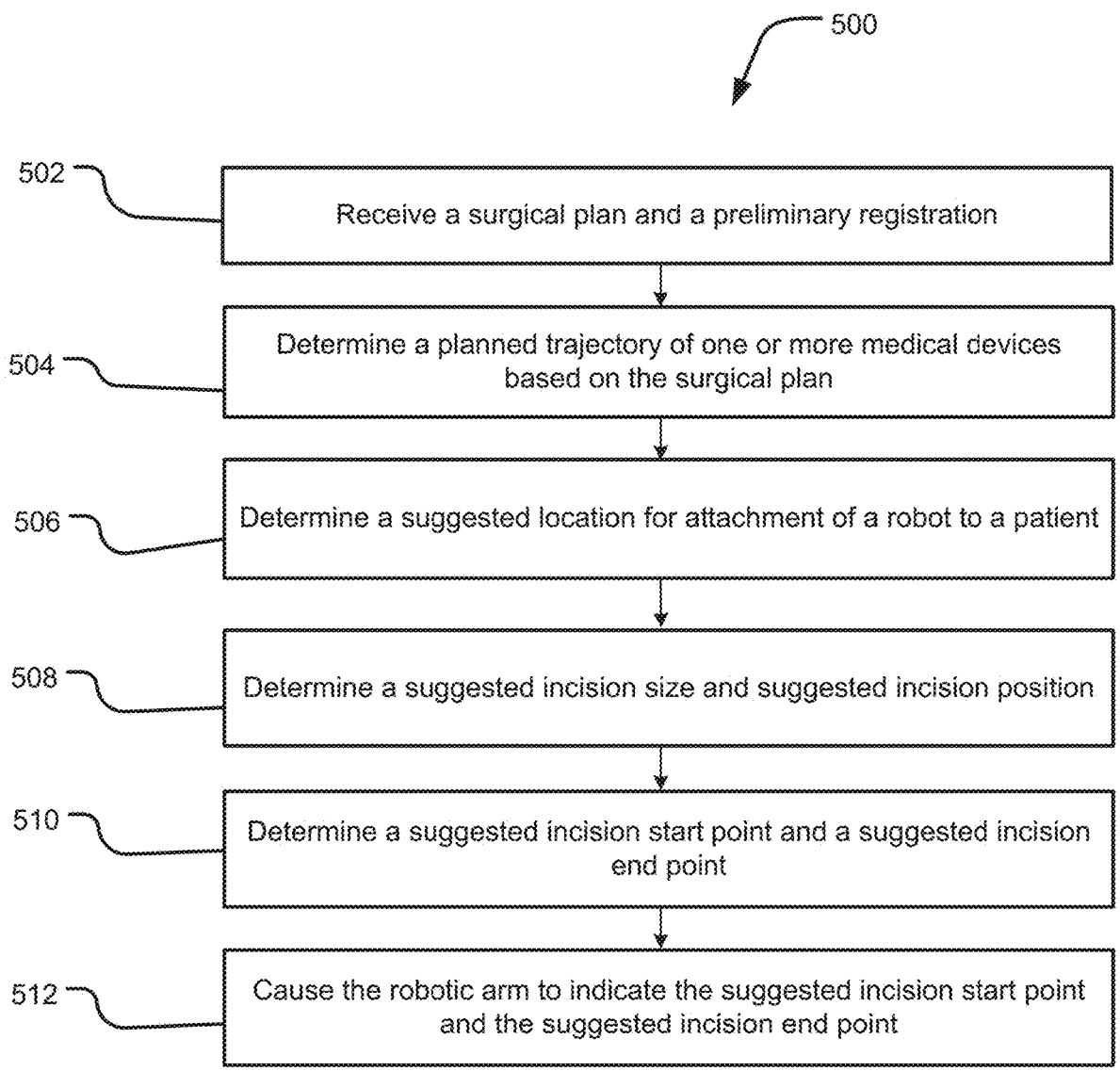
FIG. 5 is another flowchart of a method according to at least one embodiment of the present disclosure.

Turning now to FIG. 5, a method 500 for determining an incision size and location may be executed in whole or in part, for example, on a computing device such as the computing device 102 or similar device, and may utilize one or more other components of the system 100 or similar components. One or more aspects of the method 500 may be performed by or with a surgical robot, a surgeon, or a combination of both using one or more imaging devices such as the imaging device 112 or 212.

The method 500 may comprise receiving a surgical plan, which may be the same as or similar to the surgical plan 122, and a preliminary registration (step 502). The surgical plan and/or the preliminary registration may be received via a user interface such as the user interface 110 or 216 and/or via a communication interface such as the communication interface 108 of a computing device such as the computing device 102, and may be stored in a memory such as the memory 106 of the computing device 102. The preliminary registration may be based on the methods 300 or 400. The surgical plan may include information about one or more planned movements of a tool held by the robotic arm during a surgical procedure. The information may also include a timeline or schedule of the one or more planned movements. The one or more planned movements may include one or more of timestamps, a type of movement (e.g., translational and/or rotational), a duration of the movement, and/or positional information (e.g., coordinates and/or orientation).

In some embodiments, the method 500 may comprise determining information about one or more needed movements of the tool during a surgical procedure outlined or otherwise described in a surgical plan. In such embodiments, the surgical plan may not include receiving any such information via a computing device, but a processor, executing instructions stored in a memory, may generate such information based on the surgical plan.

The method 500 may also comprise determining a planned trajectory of one or more medical devices (e.g., medical tools, medical screws, medical plates, other implants) based on the surgical plan (step 504). In such embodiments, the planned trajectory may comprise a suggested depth of insertion and a suggested angle of insertion for each of the one or more medical devices.

The method 500 may also include determining a suggested position of a robot, such as robot 126 for example, so as to ensure that the robot can achieve the planned trajectory for each of the one or more medical devices (step 506). The suggested position of the robot may be a suggested position to attach the robot to an operating table such as the operating table 210. The determining step 506 may be further based on a dimensional reach of the robot, such that the suggested position of the robot ensures that the robot can achieve the planned trajectories within the dimensional reach of the robot.

The method 500 may also comprise determining a suggested incision size and suggested incision position based on the surgical plan and the preliminary registration (step 508). For example, using trajectory information in the surgical plan or calculated based on the surgical plan, as well as the suggested robot position and/or other information determined from the preliminary registration, a processor such as the processor 104 may be used to determine a suggested incision size and position that will enable the robot, when placed at the suggested robot position, to achieve any needed trajectories. In some embodiments, the suggested incision size may be, for example, the minimum size of incision needed to achieve any needed trajectories given the suggested robot position.

The method 500 may also comprise determining a suggested incision start point and a suggested incision end point based on the planned trajectory and the suggested incision size (step 510). In some embodiments, the determining of the suggested incision start point and suggested incision end point may take into account the suggested robot position and/or information about a dimensional reach of the robot. The suggested incision start point and end point may also be determined based on information in a surgical plan, including information about the anatomical features of the patient. For example, a suggested incision start point and end point may be determined to avoid making an incision directly over an anatomical feature (e.g., a bone, an organ, an artery) that cannot or should not be cut.

The method 500 may also comprise causing a robotic arm, such as robotic arm 128, to indicate the suggested incision start point and the suggested incision end point (step 512). In some embodiments, the robotic arm may be caused to indicate the suggested incision start point and the suggested incision end point in sequence. In other embodiments, the robot comprises a first robotic arm and a second robotic arm and the method 500 further comprises causing the first robotic arm to indicate the suggested incision start point and the second robotic arm to indicate the suggested incision end point, whether simultaneously or in sequence. Whether the suggested incision start point and suggested incision end point are indicated by one or two robotic arms, each point may be marked using a marker. The marker may be, for example, but not limited to, a laser, an ink marker, an adhesive mark, or the like. The marker for the suggested incision start point may be the same as or different from the marker for the suggested incision end point. In other embodiments, the robotic arm may simply move a distal end thereof (which may or may not comprise an end effector) directly over the suggested incision start point and/or the suggested incision end point, so as to indicate the point but without using a marker.

Although described herein in connection with a robot that connects to an operating table, the method 500 may be used in connection with repositionable robots of any kind, including robots that are supported on a selectively moveable cart, robots supported entirely by a patient's body, and robots that may be selectively connected to a structure other than an operating table The methods and systems described herein provide a preliminary registration that determines an optimized or recommended robot positioning for a surgical procedure. The robot positioning ensures that a robot arm of the robot can reach each point of interest during the surgical procedure, thereby reducing or eliminating the risk for re-positioning the robot during the surgical procedure. The methods and systems also provide for a tracking device capable of placement on a non-sterile surface of a patient that is easy and simple to place and remove from the patient. Thus, methods and systems for performing a preliminary registration using the tracking device as described herein provide for a quick and easy preliminary registration process that provides valuable information to optimize positioning of a robot on an operating table and/or a patient.

As may be appreciated based on the foregoing disclosure, the present disclosure encompasses methods with fewer than all of the steps identified in FIGS. 3, 4, and 5 (and the corresponding description of the methods 300, 400, and 500), as well as methods that include additional steps beyond those identified in FIGS. 3, 4, and 5 (and the corresponding description of the methods 300, 400, and 500). One or more steps of the methods described herein may be performed in an order other than the order in which they are described herein.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for preliminary registration, comprising:
a tracking device configured to be positioned on a non-sterile surface of a patient's skin;
at least one processor; and
at least one memory storing instructions for execution by the at least one processor that, when executed, cause the at least one processor to:
receive a surgical plan corresponding to a planned surgical procedure;
receive image data corresponding to an image depicting the tracking device configured to be positioned on the non-sterile surface of the patient's skin and an anatomical element of the patient;
receive robot positional data corresponding to a position of a robot;
locate the robot and the anatomical element in a common three-dimensional (3D) coordinate system based on the image data and the positional data to yield a preliminary registration;
determine a suggested robot position based on the location of the robot in the 3D coordinate system, a dimensional reach of the robot, and the surgical plan; and
position the robot based on the suggested robot position.

2. The system of claim 1, wherein the image data is fluoroscopic image data and the image is two-dimensional.

3. The system of claim 1, wherein the tracking device comprises a fluoroscopy marker and a fiducial marker.

4. The system of claim 1, wherein the memory stores further data for processing by the processor that, when processed, causes the processor to:
identify a patient position based on the preliminary registration.

5. The system of claim 1, wherein the surgical plan includes a planned trajectory of one or more medical devices, the planned trajectory comprising a suggested depth of insertion and a suggested angle of insertion for each of the one or more medical devices, and wherein the determining is further based on the surgical plan.

6. The system of claim 5, wherein the memory stores further data for processing by the processor that, when processed, causes the processor to:
determine a suggested incision start point and a suggested incision end point based on the planned trajectory and the suggested incision size.

7. The system of claim 1, wherein the image data corresponds to a single image.

8. The system of claim 1, wherein the memory stores further data for processing by the processor that, when processed, causes the processor to:
determine a suggested location for attachment of the robot to the patient based on the preliminary registration and the surgical plan.

9. The system of claim 1, wherein the memory stores further data for processing by the processor that, when processed, causes the processor to:
determine a suggested incision size and suggested incision position based on the preliminary registration and the surgical plan.

10. The system of claim 1, further comprising:
a robot, wherein the robot comprises the robotic arm and a second robotic arm.

11. The system of claim 10, wherein the memory stores further data for processing by the processor that, when processed, causes the processor to:
cause the robotic arm to indicate a suggested incision start point and the second robotic arm to indicate a suggested incision end point.

12. A system for preliminary registration, comprising:
a tracking device configured to be positioned on a non-sterile surface of a patient's skin;
at least one processor; and
at least one memory storing instructions for execution by the at least one processor that, when executed, cause the at least one processor to:
receive image data corresponding to an image depicting the tracking device configured to be positioned on the non-sterile surface of the patient's skin and an anatomical element of the patient;
receive robot positional data corresponding to a position of a robot;
locate the robot and the anatomical element in a common three-dimensional (3D) coordinate system based on the image data and the positional data to yield a preliminary registration;
determine a suggested robot position based on the location of the robot in the 3D coordinate system and a dimensional reach of the robot; and
positioned the robot based on the suggested robot position.

13. The system of claim 12, wherein the tracking device comprises a fluoroscopy marker and a fiducial marker.

14. The system of claim 12, wherein the image data corresponds to a single image.

15. The system of claim 12, wherein the memory stores further data for processing by the processor that, when processed, causes the processor to:
identify a patient position based on the preliminary registration.

16. The system of claim 12, wherein the memory stores further data for processing by the processor that, when processed, causes the processor to:
receive a surgical plan having a planned trajectory of one or more medical devices, the planned trajectory comprising a suggested depth of insertion and a suggested angle of insertion for each of the one or more medical devices, and determining the suggested robot position is further based on the surgical plan.

17. The system of claim 16, wherein the memory stores further data for processing by the processor that, when processed, causes the processor to:
   determine a suggested location for attachment of the robot to the patient based on the preliminary registration and the surgical plan.

18. The system of claim 16, wherein the memory stores further data for processing by the processor that, when processed, causes the processor to:
   determine a suggested incision size and suggested incision position based on the preliminary registration and the surgical plan.

19. The system of claim 18, wherein the memory stores further data for processing by the processor that, when processed, causes the processor to:
   determine a suggested incision start point and a suggested incision end point based on the planned trajectory and the suggested incision size.

* * * * *